(12) United States Patent
Rannisto et al.

(10) Patent No.: US 9,696,284 B2
(45) Date of Patent: Jul. 4, 2017

(54) EXTRACTION COLUMN

(71) Applicant: Thermo Fisher Scientific Oy, Vantaa (FI)

(72) Inventors: Joni Rannisto, Kerava (FI); Kelly Flook, San Leandro, CA (US); Leena Valmu, Helsinki (FI); Ville Saarainen, Espoo (FI); Suvi Ravela, Helsinki (FI); Johan Finell, Vantaa (FI)

(73) Assignee: Thermo Fisher Scientific Oy, Vantaa (FI)

( * ) Notice: Subject to any disclaimer, the term of this patent is extended or adjusted under 35 U.S.C. 154(b) by 82 days.

(21) Appl. No.: 14/735,900

(22) Filed: Jun. 10, 2015

(65) Prior Publication Data
US 2016/0363565 A1 Dec. 15, 2016

(51) Int. Cl.
*G01N 30/60* (2006.01)
*G01N 1/40* (2006.01)
(Continued)

(52) U.S. Cl.
CPC .......... *G01N 30/6052* (2013.01); *G01N 1/40* (2013.01); *G01N 1/405* (2013.01); *G01N 2030/009* (2013.01); *G01N 2035/1053* (2013.01)

(58) Field of Classification Search
CPC ............... G01N 30/60; G01N 30/6004; G01N 2030/6013; G01N 30/6026;
(Continued)

(56) References Cited

U.S. PATENT DOCUMENTS 5,334,310 A    8/1994    Frechet et al.
5,439,593 A    8/1995    Price
(Continued)

FOREIGN PATENT DOCUMENTS

EP    1235905 A2    9/2002
WO    0142487 A2    6/2001

OTHER PUBLICATIONS

ProSwift® Reversed Phase Monolithic Column Product Manual, DIONEX® Corporation, Document No. 065123, Revision 03, Mar. 2009, now sold under the Thermo Scientific brand (48 pages).
(Continued)

*Primary Examiner* — Michael A Lyons
*Assistant Examiner* — Philip Cotey
(74) *Attorney, Agent, or Firm* — Wood Herron & Evans LLP

(57) ABSTRACT

Described are extraction columns and systems that include extraction columns. The extraction column includes a column body that has a reservoir portion, an extraction media portion, and a collar portion. The reservoir portion includes an inlet and a reservoir. The extraction media portion includes an elongated sleeve having an inner surface defining a cavity. The extraction media portion has an inlet end in fluid communication with the reservoir and an outlet end. An extraction medium is disposed in the cavity of the elongated sleeve. The collar portion extends axially in a common direction with the elongated sleeve. The collar portion has a terminal end which is spaced apart from the outlet end of the elongated sleeve and which extends axially at least to a plane defined by the outlet end of the elongated sleeve.

34 Claims, 10 Drawing Sheets

(51) Int. Cl.
*G01N 30/00* (2006.01)
*G01N 35/10* (2006.01)

(58) Field of Classification Search
CPC ............. G01N 30/6052; G01N 30/606; G01N 30/6086; G01N 30/6091; G01N 30/6095; G01N 30/7233
USPC ........................................................ 73/61.53
See application file for complete search history.

(56) References Cited

U.S. PATENT DOCUMENTS

| | | | |
|---|---|---|---|
| 5,633,290 | A | 5/1997 | Frechet et al. |
| 5,918,273 | A | 6/1999 | Horn |
| 6,566,145 | B2 | 5/2003 | Brewer |
| 6,783,672 | B2 | 8/2004 | Tubbs et al. |
| 7,409,880 | B2 | 8/2008 | Hale et al. |
| 7,482,169 | B2 | 1/2009 | Gjerde et al. |
| 7,922,908 | B2 | 4/2011 | Allington et al. |
| 2003/0087454 | A1* | 5/2003 | Schultz .................. B01L 3/0275 436/161 |
| 2004/0084375 | A1* | 5/2004 | Hodgin .................. B01D 15/22 210/656 |
| 2006/0213824 | A1* | 9/2006 | Higgins ................. B01D 15/22 210/198.2 |
| 2009/0081083 | A1 | 3/2009 | Clark et al. |
| 2012/0037555 | A1* | 2/2012 | Lundin .................. B01D 15/22 210/198.2 |
| 2012/0214974 | A1 | 8/2012 | Dawson |

OTHER PUBLICATIONS

Flook, Kelly et al., "Reversed-phase monoliths prepared by UV polymerization of divinylbenzene", Journal of Separation Science, Jun. 10, 2011-Aug. 24, 2011, pp. 2047-2053 (XP055296722).
International Searching Authority, European Patent Office, International Search Report and Written Opinion issued in corresponding PCT Application No. PCT/FI2016/050416, mailed on Sep. 5, 2016 (13 pages).

* cited by examiner

EXTRACTION COLUMN

FIELD

The present invention relates to a device and system for extracting a component from a sample, and more particularly to a disposable tip that includes an extraction column.

BACKGROUND

Typically liquid chromatography-mass spectrometry (LC-MS) based proteomics is performed targeting peptides as analytes in a process called bottom-up proteomics. In that process, proteins are digested into peptides using proteases. The duration of the digestion can be lengthy and very often requires an overnight incubation. In the clinical setting, short sample processing time is desired. Top-down proteomics introduces an option where intact proteins can be analyzed as such using LC-MS. This type of proteomics does not require lengthy digestion, making it more desirable for clinical use as well as in automated systems. However, the protein fraction must still be extracted from the other non-protein components in the sample. Proteins may be extracted from other components in a sample with an extraction column. Preferably, such extraction columns would allow automated sample preparation and integration directly into LC.

Typically, pipette tips and similar consumables are sold, transported and inserted into an automated analyzer in trays or other means providing a known position and orientation for each tip. However, it is easier and less expensive to pack and transport tips in a container where the tips are packaged in bulk in random order, such as in a bag or box. Typically, pipette tips are cone-shaped with a pointed end and an open end that results in the tips stacking and piling up when loosely stored in random order and orientation. This makes it difficult for an automated system to pick up one pipette tip at a time and piled tips could cause jams in an automated system. Another problem with this so called "random packaging" is that the delicate end of pipette tips that includes an extraction medium might be damaged by contacting other tips.

SUMMARY

Described herein are extraction columns and systems that address one or more of the problems or needs identified above. In an embodiment, the extraction column includes a column body that has a reservoir portion, an extraction media portion, and a collar portion. The reservoir portion includes an inlet and a reservoir. The extraction media portion includes an elongated sleeve having an inner surface defining a cavity. The extraction media portion has an inlet end in fluid communication with the reservoir and an outlet end disposed remote from the inlet end. An extraction medium is disposed in the cavity of the elongated sleeve. The collar portion extends axially in a common direction with the elongated sleeve. The collar portion has a terminal end which is spaced apart from the outlet end of the elongated sleeve and which extends axially at least to a plane defined by the outlet end of the elongated sleeve. In embodiments of the invention, the terminal end of the collar portion extends axially beyond the plane defined by the outlet end of the elongated sleeve, and in some alternative embodiments, the terminal end of the collar portion extends axially beyond the plane defined by the outlet end of the elongated sleeve by a distance sufficient to prevent contact of the outlet end of the elongated sleeve by any portion of a second extraction column. In embodiments of the invention, the reservoir portion inlet has an inner diameter that that is not greater than, and may be less than, the outer diameter of the terminal end of the collar portion. Embodiments of the extraction columns may optionally include a shoulder projecting outwardly from the reservoir portion adjacent the inlet. Embodiments of the extraction medium may include a solid phase extraction medium, such as a polymer monolith, or a plurality of non-porous beads, porous beads, or a mixture non-porous beads and porous beads.

Aspects of the invention are directed to systems that include embodiments of the extraction column in combination with a sample port having a first chamber configured to receive the elongated sleeve of the extraction column. The systems may optionally include a liquid delivery device, such as a ceramic probe. The systems may also optionally include an analytical device such as a mass spectrometer, a liquid chromatography device, and combinations thereof.

Various additional objectives, advantages, and features of the invention will be appreciated from a review of the following detailed description of the illustrative embodiments taken in conjunction with the accompanying drawings.

BRIEF DESCRIPTION OF THE DRAWINGS

The accompanying drawings, which are incorporated in and constitute a part of this specification, illustrate embodiments of the invention and, together with a general description of the invention given above, and the detailed description given below serve to explain the invention.

DETAILED DESCRIPTION

Figure 1:
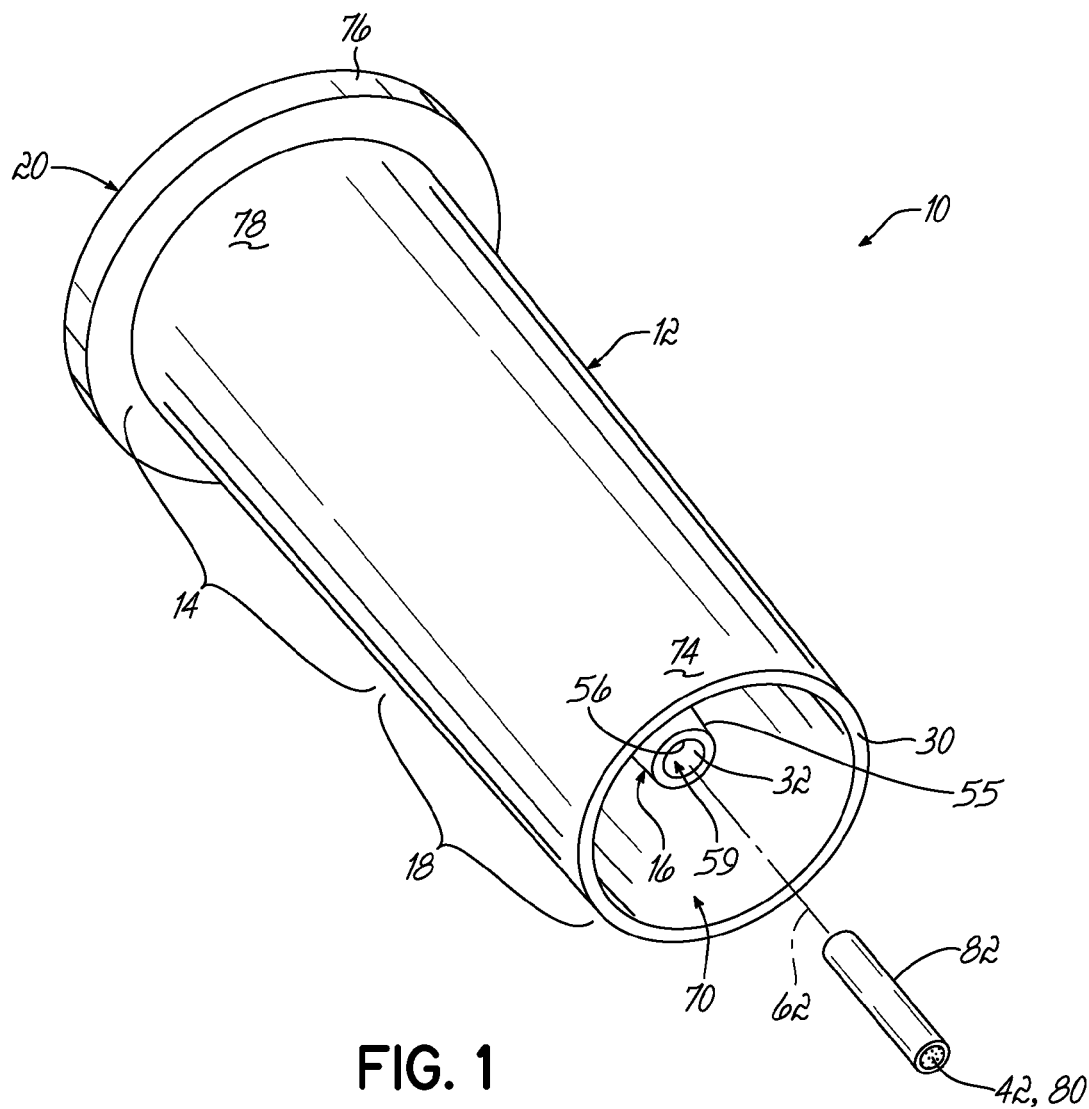
FIG. 1 is a disassembled perspective view of an extraction column in accordance with embodiments of the invention.
Figure 2:
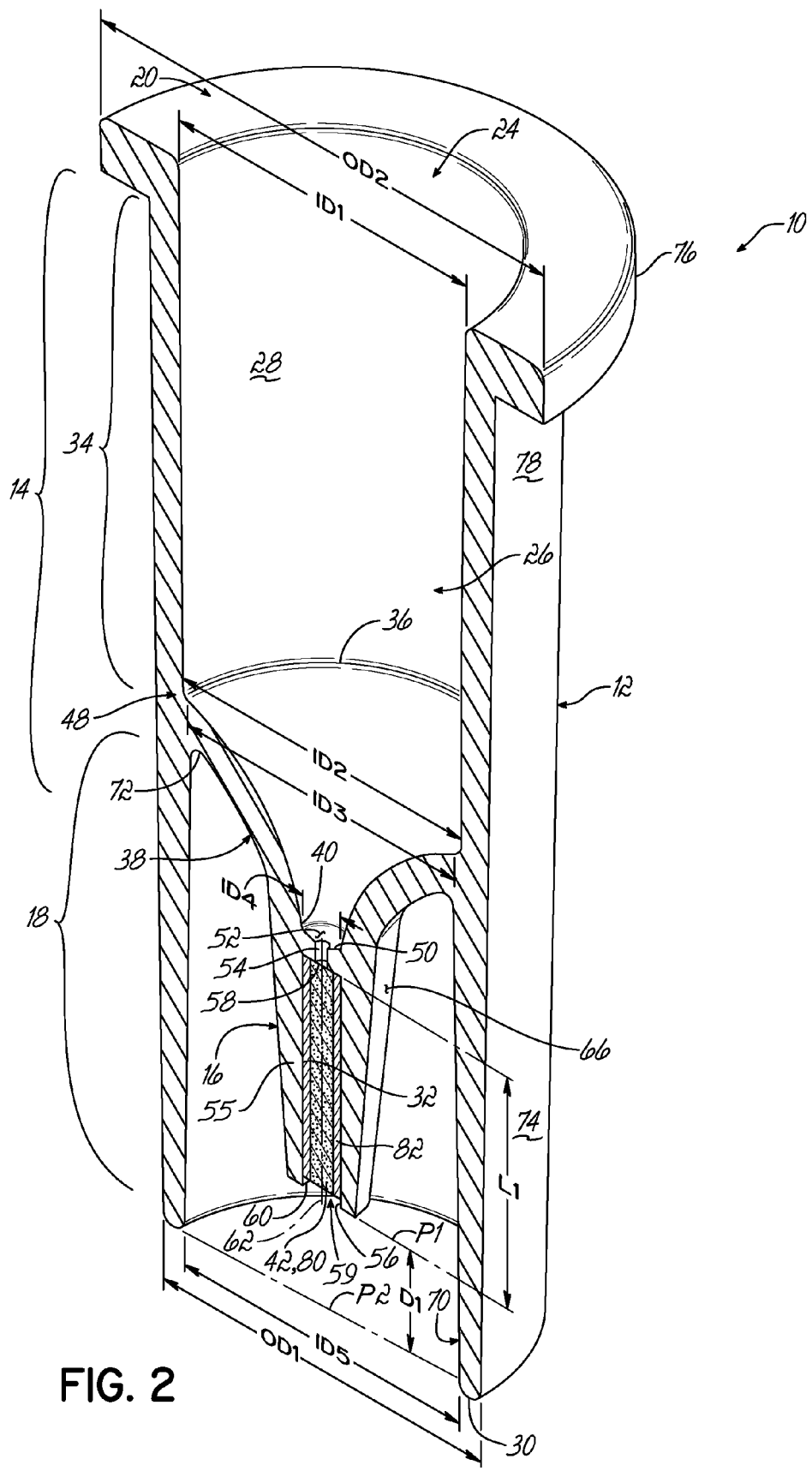
FIG. 2 is a perspective view in longitudinal cross-section of the extraction column of FIG. 1 in an assembled state.

With reference to FIGS. 1 and 2, an embodiment of the invention is directed to an extraction column 10 for extracting a component, such as protein or protein fragment, from a sample containing a mixture of components such as proteins, peptides, carbohydrates, lipids, nucleic acids, salts, and small molecules. The extraction column 10 includes a column body 12 having a reservoir portion 14, an extraction media portion 16, and a collar 18.

The reservoir portion 14 is generally located at the proximal end 20 of the column body 12 and includes an inlet 24 and a cavity that functions as a reservoir 26. The reservoir 26 is defined by the inner surface 28 of the reservoir portion 14 and is in fluid communication with the cavity 32 of the extraction media portion 16, which is generally located at the distal end 30 of the column body 12. The reservoir 26 is capable of holding a volume of liquid. In an embodiment, the volume of the reservoir 26 is sufficient to hold the volume of liquid needed to prime the extraction medium 42, the volume of the sample to be extracted, the volume of the wash solutions, and the volume of the elution solution. For example, in some extraction methods, it is necessary to dilute a sample with a suitable solvent before forcing the sample through the extraction medium 42 located in the cavity 32 of the extraction media portion 16. Typically, the step of diluting the sample is performed in a separate vessel. In the exemplary embodiment, the volume of the reservoir 26 is sufficient to dilute the sample directly in the reservoir 26 before positive pressure is applied to the reservoir 26 to transfer the sample to the extraction medium. In an embodiment of the invention, the reservoir 26 has a volume ranging from about 50 µl to about 1500 µl.

Figure 3:
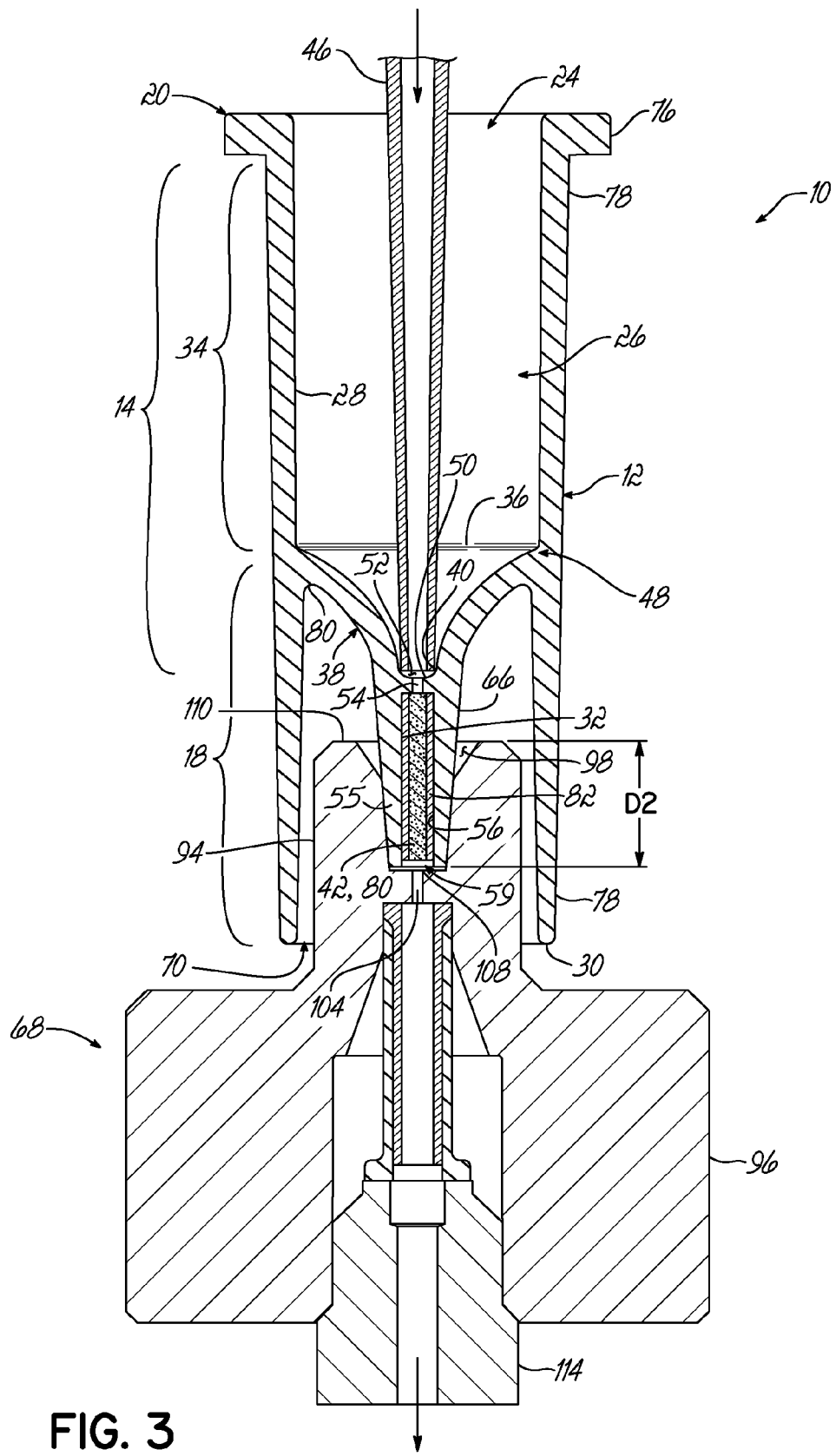
FIG. 3 is a longitudinal cross-section side view of a portion of an embodiment of a system including a liquid delivery device, an extraction column, a sample port, and a portion of an analytical device, in accordance with embodiments of the invention.

In the exemplary embodiment illustrated in FIGS. 1-3, the inner surface 28 of the reservoir 26 includes a first portion 34 proximal the inlet 24 that provides a majority of the volume of the reservoir 26 and a second portion 38 proximal the extraction media portion 16. In the exemplary embodiment illustrated in FIGS. 1-3, the inner surface 28 of first portion 34 of the reservoir 26 is generally frustoconical-shaped and has an angle of convergence between the inner diameter ID1 at the proximal end of the first portion 34 and the inner diameter ID2 at the distal end 36 of the first portion 34 that is less than about 10 degrees or, in an alternative embodiment, less than 4 degrees. As used herein, the angle of convergence is the angle between the surface referred to and the central axis of the structure, which, in the present instance, is the central axis 62 of the column body 12.

Figure 4:
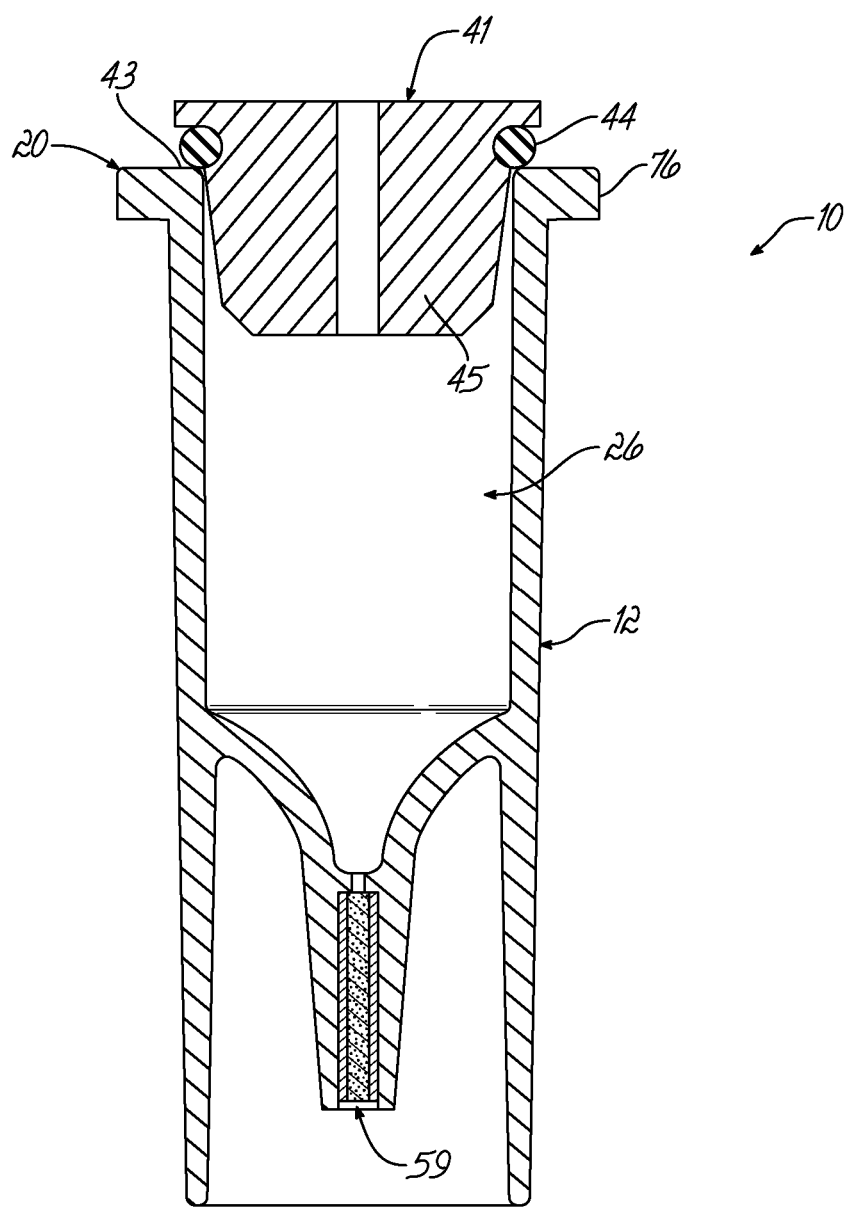
FIG. 4 is a longitudinal cross-section side view of an extraction column and a portion of an alternative liquid delivery device, in accordance with embodiments of the invention.

As illustrated in FIG. 4, the reservoir 26 may have a shape configured to be sealed against a liquid handling device 41 that can create positive air pressure in the reservoir 26 to force liquid in the reservoir 26 through the extraction medium 42. For example, the external surface 43 adjacent the proximal end 20 first portion 34 may be configured to engage and form a seal with an O-ring 44 on the mandrel 45 of a liquid handling device 41. In the alternative, the inner surface 28 of the first portion 34 of the reservoir 26 may be configured to engage and form a seal with an O-ring or external surface of the mandrel of a liquid handling device.

The second portion 38 of the reservoir 26 may be funnel-shaped and have an annular wall that tapers inwardly toward the extraction media portion 16, as illustrated in FIGS. 2 and 3. In an alternative embodiment, the second portion 38 may be frustoconical shaped. The funnel shape or frustoconical shape reduces the inner diameter of the second portion 38 and assists with guiding the end of the liquid delivery device 46 into position to form a tight seal between the liquid delivery device 46 and the extraction column 10. The second portion 38 of the reservoir 26 has an angle of convergence between the inner diameter ID3 at the proximal end 48 of the second portion 38 and the inner diameter ID4 at the distal end 50 of second portion 38. In the exemplary embodiment, the angle of convergence of the first portion 34 of the reservoir is less than the angle of convergence of the second portion 38 of the reservoir 26.

In the embodiment exemplified in FIGS. 1 to 3, the second portion 38 of the reservoir 26 includes a shelf 52 that further reduces the diameter of the reservoir 26 as it transitions into the fluid passageway 54 between the reservoir 26 and the cavity 32 of the extraction media portion 16. The shelf 52 functions as a sealing surface to form a seal with a liquid delivery device 46, such as a pipette tip or a hollow probe like a hollow ceramic probe. In some embodiments, the inner surface at the distal end of the reservoir portion may also contribute to the seal formed with the liquid delivery device 46. The seal is formed when a liquid delivery device 46, positioned as illustrated in FIG. 3, is pushed against the shelf 52 and, in some embodiments, the inner surface 40 at the distal end 50 of second portion 38 of the reservoir 26 adjacent the shelf 52, with a force sufficient to form a tight seal between the column body 12 and the liquid delivery device 46. The force applied to the liquid delivery device 46 may cause the plastic structures of the shelf 46 and/or inner surface 40 at the distal end 50 of second portion 38 of the reservoir 26 adjacent the shelf 52 to deform to the shape of the liquid delivery device 46 to create a seal between the liquid delivery device 46 and the extraction column 10. The shelf 52 in the exemplary embodiment of FIGS. 1-3 is illustrated as having a generally frustoconical shape with an obtuse angle of convergence in a range from about 45 degrees to about 90 degrees.

Figure 5:
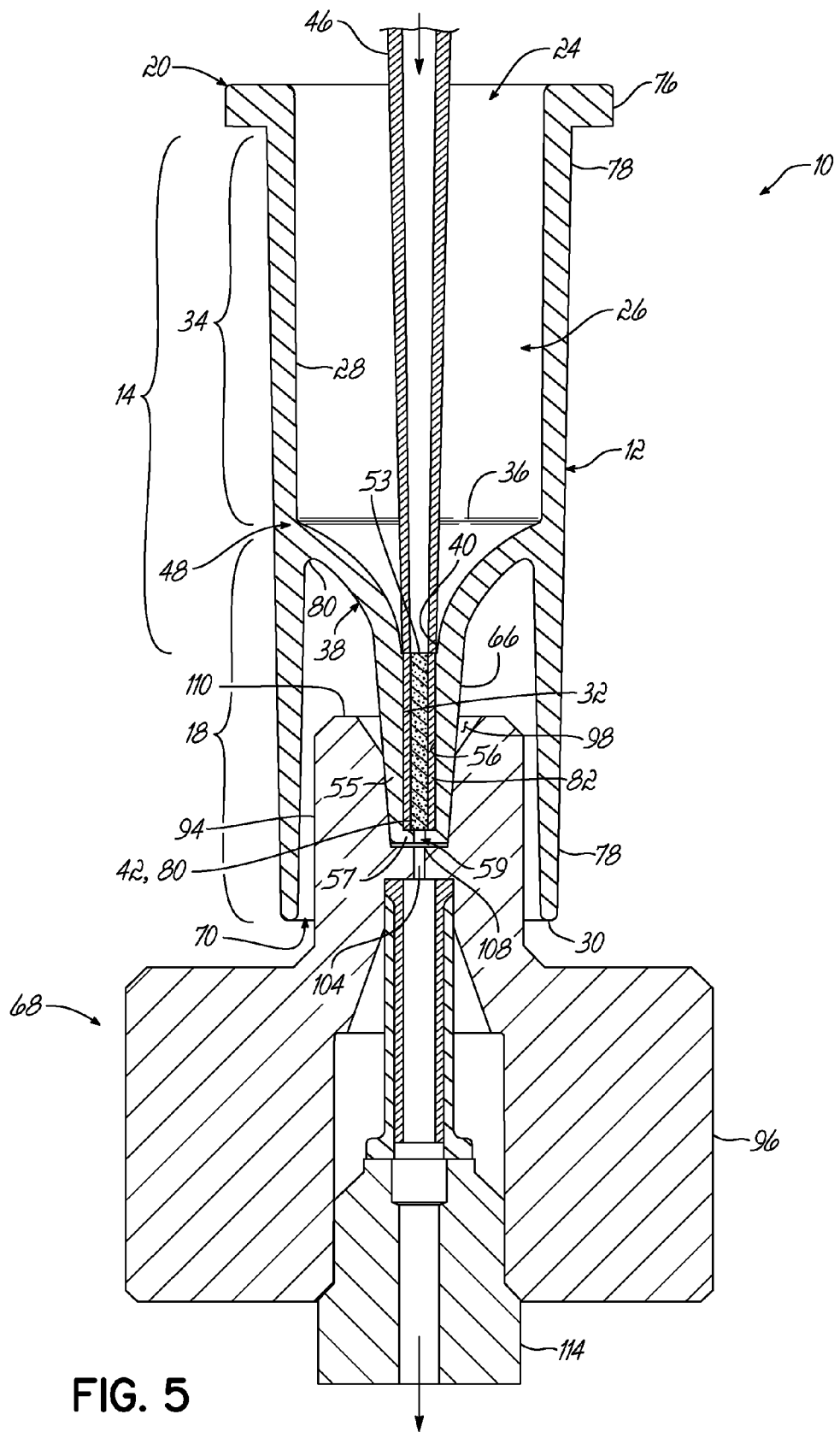
FIG. 5 is a longitudinal cross-section side view of a portion of an embodiment of a system including a liquid delivery device, an alternative embodiment of an extraction column, a sample port, and a portion of an analytical device, in accordance with embodiments of the invention.
Figure 6:
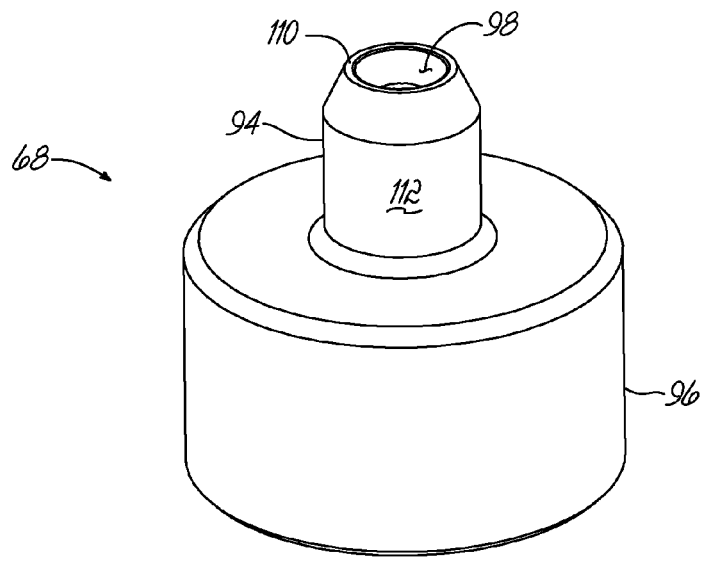
FIG. 6 is perspective view of a sample port in accordance with embodiments of the invention.
Figure 6A:
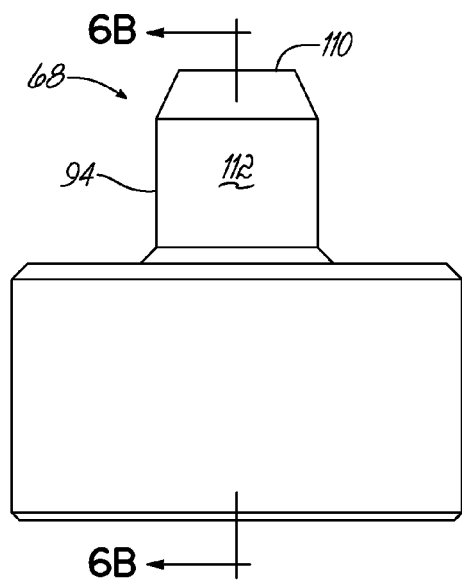
FIG. 6A is side view of the sample port of FIG. 4.
Figure 6B:
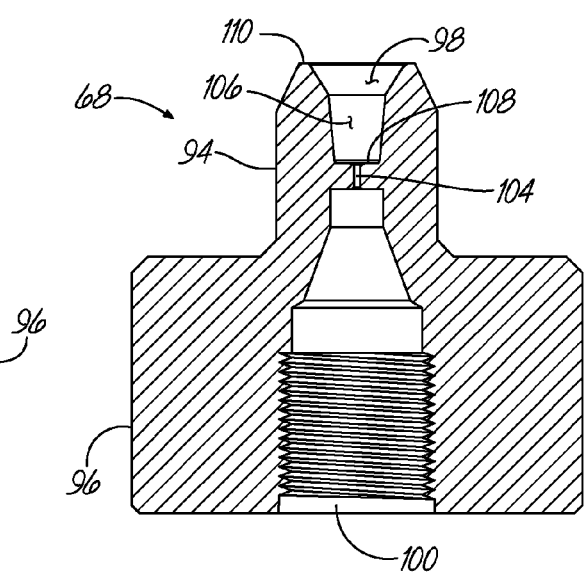
FIG. 6B is a longitudinal cross-section side view of the sample port of FIG. 4A taken along lines 6B-6B.

In an alternative embodiment illustrated in FIG. 5, the second portion 38 lacks a shelf and instead transitions directly to the cavity 32 of the extraction media portion 16. In this exemplary alternative embodiment, the liquid delivery device 46 forms a seal against the proximal end 53 of the extraction medium 42. The inner surface 40 at the distal end 50 of second portion 38 may engage a portion of the liquid delivery device 46 and contribute to the seal between the liquid delivery device 46 and the extraction medium 42. In this alternative embodiment, a shelf 57 is positioned at the outlet end 60 of the cavity 32 of the elongated sleeve 55 of the extraction media portion 16 of the column body 12. The shelf 57 reduces the inner diameter of the opening 59 of the outlet end 60 of the cavity 32 elongated sleeve 55.

In an embodiment, the seal formed between the liquid delivery device 46 and the extraction column 10 allows leakage of no more than about 10% of the volume of the sample being transferred from the liquid delivery device 46 to the extraction column 10. In another embodiment, the seal formed between the liquid delivery device 46 and the extraction column 10 allows leakage of no more than about 10% of the volume of the sample being transferred from the liquid delivery device 46 to the extraction column 10 under injection pressures ranging from about 70 bar to about 200 bar.

The embodiment illustrated in FIGS. 2-4 includes a fluid passageway 54 between the reservoir 26 and the cavity 32 of the extraction media portion 16. In this exemplary embodiment, the fluid passageway 54 is frustoconical-shaped and the angle of convergence is typically less than about 10 degrees, and in an alternative embodiment, is less than about 1 degree. The fluid passageway 54 has a length and internal diameter that minimizes the volume of the fluid passageway 54 while at the same time provides sufficient flow to prevent a buildup of backpressure caused by a restricting flow through the fluid passageway 54. The volume of the fluid passageway 54 is minimized to minimize the dead volume in the extraction column. In an embodiment, the volume of the fluid passageway 54 does not exceed about 1000 nl and may be in a range from about 1 nl to about 50 nl.

The extraction media portion 16 includes an elongated sleeve 55 having an inner surface 56 defining a cavity 32 with an extraction medium 42 disposed therein. The cavity 32 includes an inlet end 58 in fluid communication with the reservoir 26 and an outlet end 60 having an opening 59 disposed remote from the inlet end 58. In an embodiment, the cavity 32 is frustoconical-shaped with an angle of convergence of less than about 5 degrees, and in an alternative embodiment, the angle of convergence may range from about 0.2 degrees to 1 degrees. In another alternative embodiment, the angle of convergence of the frustoconical-shaped cavity 32 may be about 0.4 degrees. In embodiments having a frustoconical-shaped cavity 32, the larger diameter end of the cavity 32 opens toward the insertion point for the extraction medium 42. The internal diameter of the cavity 32 for the alternative embodiment also ranges from about 0.5 mm to about 2.0 mm, and preferably from about 0.75 mm to about 0.85 mm. The column body 12 has a central axis 62 that extends through the cavity 32 of the extraction media portion 16. The cavity 32 has a length L1 along the central axis 62 between the inlet end 58 and the outlet end 60. In an embodiment, the length L1 of the cavity 32 is in a range from about 1 mm to 10 mm. In another embodiment, the length L1 of the cavity 32 is in a range from about 3 mm to about 5 mm and is preferably in a range from about 3.5 mm to about 4.5 mm. In an embodiment, the length L1 of the cavity corresponds with the length of the elongated sleeve 55.

The extraction media portion 16 also has an external surface 66, the bottom portion of which is configured to form a seal with a sample port 68 of a sample analysis system (FIG. 3). In an embodiment, the external surface 66 has a generally frustoconical shape that is narrower at the outlet end 60 of the elongated sleeve 55. The elongated sleeve 55 may have an outside diameter at the outlet end 60 that ranges from about 1 mm to about 2 mm. In another embodiment, the elongated sleeve 55 has an outside diameter at the outlet end 60 that ranges from about 1.2 mm to about 1.5 mm. In another embodiment, the elongated sleeve 55 has an outside diameter at the outlet end 60 that is about 1.4 mm. The external surface 66 of the elongated sleeve 55 may have an angle of convergence ranges from about 1 degree to about 20 degrees and preferably, the angle of convergence ranges from about 5 degrees to about 15 degrees. In embodiments of the elongated sleeve 55, the thickness of the wall forming the elongated sleeve 55 increases from the outlet end 60 of the cavity 32 to the inlet end 58 of the cavity 32.

The collar 18 of the column body 12 extends axially in a common direction with the elongated sleeve 55. In the embodiment illustrated in FIGS. 1-4, the collar 18 has a closed end 72 that is coupled to the external surface 78 of the reservoir portion 14 adjacent the transition between the first and second portions 34, 38. In the illustrated embodiment, the external surface 74 of the collar 18 is continuous with the external surface 78 of the reservoir portion 14. The external surfaces 78, 74 of the reservoir portion 14 and the collar 18 may be tapered with an angle of convergence of less than 15 degrees, and in an alternative embodiment, in a range from about 0.1 degree to about 5 degrees.

The collar 18 has an open terminal end 70 that is spaced apart from the outlet end 60 of the elongated sleeve 55. The outlet end 60 of the elongated sleeve 55 defines a plane P1. The terminal end 70 of the collar 18 defines a plane P2 that extends at least to the plane P1 defined by the outlet end 60 of the elongated sleeve 55. In an embodiment, the plane P2 of the terminal end 70 of the collar 18 extends beyond plane P1 of the outlet end 60 of the elongated sleeve 55. In the embodiment illustrated in FIGS. 1-4, the plane P2 of the terminal end 70 of the collar 18 extends beyond plane P1 of the outlet end 60 of the elongated sleeve 55 by a distance D1 sufficient to prevent contact of the outlet end 60 of the elongated sleeve 55 by any portion of a second extraction column. For example, the distance D1 may range from about 0.1 mm to about 2 mm, which, depending on the inner diameter ID5 at the terminal end 70 of the collar 18 and the smaller of the outer diameter OD1 at the terminal end 70 of the collar 18 or the outer diameter OD2 at the proximal end 20 of the column body 12, may be sufficient to prevent contact of the outlet end 60 of the elongated sleeve 55 by any portion of a second extraction column. This structure prevents the damage to the outlet end 60 of the elongated sleeve 55 when the extraction columns 10 are loosely stored in a bag or box. An additional benefit of the plane P2 extending beyond plane P1 is that it prevents contamination of the outlet end 60 of the elongated sleeve 55 when the extraction column 10 is being handled by an automated sample analysis system. For example, a method of transporting extraction columns 10 in automated analysis systems is to have the extraction column 10 drop through a guiding pipe or hose from one location in the system to another location. If the outlet end 60 of the elongated sleeve 55 is exposed, i.e., not protected by a collar 18, there is a significant risk of carryover contamination of the outlet end 60 if the outlet end 60 contacts the surfaces of the transporting pipe or hose. The collar 18 of the present invention protects the outlet end 60 of the elongated sleeve from contacting the surfaces of the transporting hose and thereby diminishes the risk of carryover contamination between different extraction columns transported in the same hose.

The terminal end 70 of the collar 18 has an outer diameter OD1 and the inlet 24 of the reservoir 26 has an inner diameter ID1 such that the terminal end 70 of the collar 18 may not be fully inserted into the inlet 24 of the reservoir 26. In an embodiment, the inner diameter ID1 of the inlet 24 of the reservoir is not greater than the outer diameter OD1 of the terminal end 70 of the collar 18. In another embodiment, the inner diameter ID1 of the inlet 24 of the reservoir is less than the outer diameter OD1 of the terminal end 70 of the collar 18. Similarly, the proximal end 20 of the column body 12 has an outer diameter OD2 and the open terminal end 70 of the collar 18 has an inner diameter ID5 such that the proximal end 20 of the column body 12 may not be fully inserted into the open terminal end 70 of the collar 18. In the embodiment illustrated in FIGS. 1-4, the outer diameter OD2 at the proximal end 20 of the column body 12 includes an optional shoulder 76. In an embodiment, the inner diameter ID5 of the open terminal end 70 of the collar 18 is not greater than the outer diameter OD2 of the proximal end 20 of the column body 12. In another embodiment, the inner diameter ID5 of the open terminal end 70 of the collar 18 is less than the outer diameter OD2 of the proximal end 20 of the column body 12. When multiple extraction columns 10 are stored together with random packaging, such as in a bag or box, the extraction columns 10 will not stack one inside the other as would happen if one end of the extraction column were capable of fitting inside an opening in an end of a second extraction column. This aspect of the extraction columns 10 makes it significantly easier for an automated system to pick up one extraction column 10 at a time and allows the extraction columns 10 to be utilized with automated systems without being sorted and placed into racks. Therefore the extraction columns 10 can be packed, sold, stored and inserted to the an automated analytical system in loose batches without the need to pack them in specified positions and specified orientation in a rack or tray thereby improving efficiency and saving money, space and labor.

In the embodiment illustrated in FIGS. 1-4, the proximal end 20 of the column body 12 includes an optional shoulder 76 projecting outwardly from the external surface 74 of the reservoir portion 14 adjacent the inlet 24. The shoulder 76 increases the outer diameter of the proximal end 20 of the column body 12 and provides a surface that may be used as by automated devices to hang the extraction column 10 during handling or if it is desired to hang the extractions column 10 in a tray or rack system.

The extraction medium 42 is disposed in the cavity 32 of the extraction media portion 16. The extraction medium 42 allows for the extraction of a desired component from a mixed sample. The extraction medium 42 may chromatographically separate proteins from other components in a mixed biological sample. Embodiments of the extraction medium 42 are capable of reversibly binding small molecules or macromolecules such as peptides and proteins having a molecular weight that range from about 1 kDa to about 200 kDa. The extraction medium 42 may be capable of reversibly binding at least 1 µg of protein in a sample volume that ranges from about 10 µl to about 100 ml when the sample is passed through the extraction medium 42 at a flow rate in the range of about 50 µl/min to 200 µl/min. The extraction medium 42 may also elute the desired component based on a desired characteristic such as the molecular weight of the component, hydrophobicity, charge, or the affinity of the component for an aspect of the extraction medium 42. In an embodiment, the extraction medium 42 is capable of eluting at least 20% of the proteins bound from the mixed sample when eluted at a flow rate ranging from about 0.1 µl/min to about 20 µl/min with a volume of elution solvent ranging from about 1 µl to about 100 µl.

In an embodiment, the extraction medium 42 is a solid phase extraction medium and, more particularly, a porous monolith medium 80 having high internal porosity that allows sufficient flow of a sample through the porous monolith medium 80 without generating undesirable high backpressures. In an embodiment, the backpressure does not exceed about 5 bar at a flow rate of 200 µl/min. The porous monolith medium 80 is preferably capable of withstanding at least 200 bar. A benefit of the pore structure of the porous monolith medium 80 is that it results in a tortuous path for the sample that allows for rapid convective mass transfer at fast flow rates. Also, a porous monolith medium 80 does not require a frit to retain its position within the column body 12.

The porous monolith medium 80 may be prepared as a continuous bed inside of a sheath, such as a section of tubing 82. The result is that upon cutting the tubing 82 into sections, the porous monolith medium 80 is present in the full length of a microcolumn that functions as the extraction medium 42.

In the embodiment illustrated in FIGS. 1-4, the extraction medium 42 is a porous monolith medium 80 that is inserted into the cavity 32 of the extraction media portion 16 of the column body 12 from the outlet end 60 of the elongated sleeve 55 of the extraction media portion 16. In the embodiment illustrated in the FIG. 5, the extraction medium 42 is a porous monolith medium 80 that is inserted into the cavity 32 of the extraction media portion 16 of the column body 12 from the inlet end 58 of cavity 32 due to the presence of the shelf 57 at the outlet end 60 of the elongated sleeve 55. A benefit of preparing the porous monolith medium 80 inside tubing 82 and cutting the tubing 82 to form a microcolumn is that this method avoids the formation of a semi permeable or non porous layer at the boundary between the air and the polymerizing porous monolith medium, such as occurs when the porous monolith medium is allowed to polymerize directly inside of a pipette tip. The semi permeable or non porous layer can adversely affect the flow characteristics of the resulting porous monolith medium. In embodiments in which the porous monolith medium is formed directly inside the cavity 32 of the extraction media portion 16, the adverse effects of the semi permeable or non porous layer may be decreased by forming a passageway through the center of the porous monolith medium to increase the flow rate of the sample through the extraction medium. However, a high proportion of the component to be captured may remain in the passageway and bypass the porous monolith medium thereby requiring multiple passes of the sample through the medium for maximum extraction. In contrast, preparing the porous monolith medium 80 inside tubing 82 which is cut into segments produces a porous cylinder where the pore structure and porosity is uniform across the diameter and along the length of the porous monolith medium 80. This preparation process results in the flow of a sample through the porous monolith medium 80 unhindered by semi permeable or non porous surfaces and results in substantially uniform binding across the porous monolith medium 80 to provide maximal extraction of the desired component in a single pass through the porous monolith medium 80.

Tubing 82 on the outside of the porous monolith medium 80 provides a protective layer that aids with handling the porous monolith medium 80. For example, during the manufacture of the extraction column 10, the column body 12 may be formed independently of the porous monolith medium 80. The porous monolith medium 80 is then inserted into the cavity 32 of the extraction media portion 16 of the column body 12. In embodiments in which the porous monolith medium 80 formed in a section of tubing 82, the tubing 82 allows the porous monolith medium 80 to be more easily handled for insertion into the cavity 32 of the extraction media portion 16. In addition, when the porous monolith medium 80 is inserted into the cavity 32 of the reservoir portion 14, the wall of the tubing 82 may act as a support for the porous monolith medium 80 and may act as a sealing surface against the inner surface 56 of the cavity 32 to prevent back flow around the porous monolith medium 80.

When the porous monolith medium 80 formed in a section of tubing 82 is inserted into the cavity 32 of the reservoir portion 14, the tubing 82 compresses around the porous monolith medium 80 to prevent the porous monolith medium 80 from being extruded from the tubing 82.

The porous monolith medium 80 may optionally be coupled to the inner surface of the tubing 82 to improve resistance to extrusion of the porous monolith medium 80. For example, the inner surface of the tubing 82 may be treated to create covalent bond attachment points for the polymerizing porous monolith medium 80. To activate the inner surface of a tubing such as polyethylene ether ketone (PEEK) tubing, the interior of the tubing may be filled with reaction solution containing a solvent such as acetonitrile or propionitrile (alkyl nitrile derivatives) and an azo-class initiator such as Vazo-64 or Vazo-55 in a concentration from about 1% to about 10% (volume). The filled tubing may then be heated to a minimum of 80% of the solvent's 10-hour half life temperature, for example Vazo-64 has a 10-hour decomposition half life at 64 degrees Celsius. The reaction may be allowed to proceed for at least 30 minutes. The reaction solution may be replaced with fresh reaction solution and allowed to proceed for an additional duration of at least 30 minutes. In an embodiment, the ends of the tubing are sealed generating an internal backpressure of at least 5 psi. In another embodiment, the reaction solution is continuously replenished at ambient pressure. The reaction solution is then removed from the tubing and the tubing is allowed to dry with a stream of nitrogen. After drying, the polymerization mixture is injected into the lumen of the activated tubing. During polymerization of the porous monolith medium 80, the activated attachment points on the inner surface of the tubing are incorporated into the extraction medium.

While PEEK tubing is used as the exemplary tubing, other types of polymeric tubing may be used including cyclic olefin copolymers ("COC") and fluoro-polymers such as ethylene tetrafluoroethylene (ETFE), fluorinated ethylene propylene (FEP) and other fluoro-polymers. Additionally, fused silica tubing may be used and is activated by covalently binding an acrylate- or methacrylate-containing silanization reagent after hydrolysis of the fused silica.

The tubing 82 may have an inner diameter that ranges from about 0.1 mm to about 1 mm. In an embodiment, the inner diameter of the tubing 82 ranges from about 0.4 mm to about 0.6 mm. In another embodiment, the inner diameter of the tubing is about 0.5 mm. The tubing 82 with porous media formed inside may be cut to a length that, when combined with the inner diameter of the tubing, provides the desired volume for the porous extraction media. In an embodiment, the length of the tubing 82 with porous monolith medium 80 is cut into sections ranging from about 6 mm to about 2 mm and in an alternative embodiment, the length ranges from about 3 mm to about 5 mm or is about 4 mm. After the porous extraction medium polymerizes, the tubing may be cut to the desired length with a tubing cutter such as an IDEX A-350 tubing cutter.

The porous monolith medium 80 may be prepared by polymerization of a mixture that includes suitable monomers in the presence of an initiator and a pore-forming solvent (porogen). The resulting porous monolith medium 80 has pores ranging in diameter from about 50 nm to about 20,000 nm. The porous monolith medium 80 may have pores in the range of about 50 nm-200 nm or about 750-10000 nm. The porous monolith medium 80 may be polymer globules having a diameter that ranges from about 20 nm to about 10,000 nm. The porous monolith medium 80 should be capable of withstanding at least about 200 bar pressure.

The monomers may be selected from vinyl containing monomers, acrylate containing monomers, methacrylate containing monomers, acrylamide, polyolefin, polyester, polyurethane, polyamide, fluoro-substituted ethylene, and combinations thereof. The vinyl containing monomers may include vinyl aromatic monomers such as monovinyl substituted aromatic monomers and divinyl substituted aromatic monomers and combinations thereof. Exemplary vinyl aromatic monomers include divinyl benzene, styrene, alkyl substituted styrene such as ethyl vinyl benzene, alpha-methylstyrene, alkyl substituted alpha-methyl styrene, halogen substituted alpha-methyl styrene such as chloromethyl styrene and combinations thereof. The alkyl substitutions may include up to 18 carbon atoms. The acrylate containing monomers include mono-, di-, and tri-acrylates. The methacrylate monomers include mono-, di-, and tri-methacrylates such as glycidyl methacrylate, ethylene dimethacrylate, trimethylolpropane, trimethylacrylate, hydroxyethyl methacrylate. In an embodiment, the monomers, or mixtures of at least two monomers, are generally present in the polymerization mixture in an amount of from about 10 vol. % to about 60 vol. %, and in an alternative embodiment, in an amount of from about 20 vol. % to about 70 vol. %.

The porogen may be selected from a variety of different types of materials. For example, suitable liquid porogens include aliphatic hydrocarbons, aromatic hydrocarbons, esters, alcohols, ketones, ethers, solutions of soluble polymers, and mixtures thereof. Exemplary porogens include 4,4,4-trimethyl pentane, alcohols having from 1 to 12 carbon atoms, toluene, butylacetate, 1,4, butanediol, water, acetone, hexane, cyclohexane, cyclohexanol, tetrahydrofuran (THF) and combinations thereof. In an embodiment, the porogen is generally present in the polymerization mixture in an amount of from about 20 vol. % to about 90 vol %, and in an alternative embodiment, from about 60 vol. % to about 80 vol %.

The initiators may include thermal polymerization initiators, conventional free-radical polymerization initiators, photoinitiators, and redox initiators. Examples of suitable initiators include peroxides such as OO-t-amyl-O-(2ethyl-hexyl)monoperoxycarbonate, dipropylperoxydicarbonate, and benzoyl peroxide, azo compounds such as azobisisobutyronitrile (Dupont Vazo-64), 2,2'-azobis(2-amidinopropane)dihydrochloride, and 2,2'-azobis(isobutyramide)dihydrate, and ammonium persulfate and tetramethylethylenediamine (TMEDA). In an embodiment, the initiator is generally present in the polymerization mixture in an amount of from about 0.2% by weight to about 5% by weight of the monomers and in an alternative embodiment, from about 1% by weight to about 2% by weight of the monomers.

The components of the polymerization mixture are mixed in accordance with routine techniques and injected into the interior of the tubing and allowed to polymerize. For example, in an embodiment, the tubing is filled with the polymerization mixture and pressured is applied to about 100 psi. Pressurization helps prevent the formation of bubbles in the polymerization mixture as nitrogen is formed during the decomposition of the initiator during polymerization. In other embodiments, the tubing is filled with the polymerization mixture and both ends of the tubing are sealed while polymerization is allowed to proceed. Sealing both ends of the tubing results in increased pressure in the interior of the tubing as polymerization proceeds, which prevents the formation of nitrogen bubbles. In yet another embodiment, the tubing is filled with the polymerization mixture and one end of the tubing is sealed and the other end of the tubing is left open but placed in vial. The filled tubing is heated during the polymerization step. Locating the open end of the tubing in a vial allows for liquid expansion while the mixture is heated during polymerization, which prevents pressure increases caused by heating that could detrimentally affect the porosity of the porous monolith medium. In embodiments utilizing a photoinitiator, the filled tubing may be subjected to UV irradiation. Examples of porous monolith media and methods of making the same are described in U.S. Pat. No. 7,922,908, which is incorporated by reference in its entirety.

The porous monolith medium 80 may also be functionalized. For example, the porous monolith medium 80 may be prepared where the epoxide or halide functionality can be reacted with amines or sulfides to create, for example, anion exchange media or with, for example carboxylic acid, phosphoric acid, sulfonic acid to create cation exchange media. These groups may then be further modified to allow attachment of proteins, peptides or immunoglobulins to create affinity separation and extraction media. Epoxide groups may be either reacted directly with proteins, peptides or immunoglobulins or after conversion to aldehyde. Other affinity media that are possible include immobilized metal ion affinity chromatography (IMAC) phases and boronate phases.

Exemplary porous materials suitable for use as the porous monolith medium 80 and the methods of making such materials are described in U.S. Pat. Nos. 5,334,310 and 5,633,290, each of which is incorporated by reference in its entirety.

In an alternative embodiment, the extraction medium 42 may include a plurality of porous and/or non-porous beads, such as glass, silica or polymeric beads, that are contained in the cavity 32 of the extraction media portion 16. In this embodiment, the inlet end of the cavity may include a first frit and the outlet end of the cavity may include a second frit. The frits function to prevent the beads from escaping the cavity. The beads are packed into the cavity sufficient to allow for a sufficient flow rate while not creating undesirable backpressure. Exemplary beads are described in U.S. Pat. No. 6,783,672, which is incorporated by reference in its entirety.

During use, before a sample is passed through the extraction column 10, the extraction medium 42 is wetted with a wetting solvent. In embodiments wherein the extraction medium 42 includes a porous monolith medium 80, the porous monolith medium 80 is wetted with a sufficient volume of a wetting solvent that may include an organic solvent such as acetonitrile (ACN) and an aqueous component such as 0.2 vol. % formic acid (FA). Typically about 10 μl to about 100 μl of wetting solvent is used to wet the porous monolith medium 80. The porous monolith medium 80 is then equilibrated with an equilibration solvent that may include water and about 0.2 vol. % FA. Typically about 10 μl to about 100 μl of equilibration solvent is used to equilibrate the porous monolith medium 80. Samples containing compounds of interest, such as proteins, in volumes ranging from 10 μl to 100 μl are then forced through the porous monolith medium 80 in the extraction column 10. The flow through from the samples may optionally be collected for additional analysis. The porous monolith medium 80 is then washed with a wash solution that includes water and about 0.1 vol. % to about 0.2 vol. % FA. Typically about 10 μl to about 100 μl of wash solution is used to wash the sample captured in the porous monolith medium 80. The compounds captured by the porous monolith medium 80 are then eluted with an elution solution. The content of the elution solution and the volumes and elution times may vary depending on the type of elution that is desired. Where quick elution is desired, the elution solution may include water, an organic component in a range of about 20-60 vol. %, and about 0.2 vol. % FA; about 1 μl to about 100 μl of elution solution is used to elute the capture compounds from the porous monolith medium 80. The liquid solutions, including the sample, may be rapidly pushed through the extraction medium 42. Compound binding in the extraction medium 42 occurs rapidly and the elution time is dependent on the desired application. Isocratic elution or elution using fast gradients enables extremely fast performance that can be used with automated systems in circumstances where high throughput is desired. When used in combination with high-resolution mass spectrometry, it is possible to identify compounds such as proteins using fast elution. Such methods may be useful where rapid analysis is needed such as microbial identification. When more detailed analysis is desired, the elution may be performed slowly allowing the compounds to elute sequentially from the extraction column 10 according to a desired characteristic, such as molecular weight, charge, hydrophobic interaction, or other affinity-type interaction with components of the extraction column 10. The slow elution can be done with a short (e.g., about 5 minutes) or long (e.g., about 30 minutes) elution gradient. For example, in an embodiment, the percentage of organic component in the elution solvent may be increased continuously or stepwise throughout the gradient to allow for elution over a desired duration. The longer elution durations enable analysis of a single targeted compound, such as an antibiotic resistance marker in a microbial sample or a cancer biomarker from a biopsy. The possibility of applying a gradient for effective compound separation allows the user to avoid having to use an expensive and time consuming analytical column. Analytical columns are used multiple times requiring wash steps to avoid carryover from one sample to another. The present extraction column 10 may be disposable and enable the user to avoid washing steps and carryover from one sample to the next.

The eluted compounds may be collected for later analysis or, preferably, passed directly into an analysis system via a sample port 68 as described in greater detail below. Passing the eluted sample directly into the analysis system takes advantage of the ability of the extraction column 10 to quickly extract compounds from a sample and also to chromatographically elute compounds based on a desired characteristic such as by molecular weight, charge, hydrophobic interaction, or other affinity-type reactions with components of the column. An exemplary analytical system is a liquid chromatography (LC) system. When the extraction column 10 is used to elute a compound directly into an LC system, the extraction column 10 must be capable of withstanding the high pressure utilized in the LC system. In addition, the liquid flow in an LC system can be extremely low, thus the void and dead volumes need to be minimized. Embodiments of the present extraction column 10 accomplish this by positioning the extraction medium 42 between the sealing surfaces of the reservoir 26 and the outlet end 60 of the extraction media portion 16 and by minimizing the volume of the fluid passageway between the sealing surfaces and the extraction medium 42. With this configuration, the sample essentially passes directly from the extraction medium 42 into the sample port of the LC system in a minimal volume of liquid.

With reference to FIGS. 3 and 5 to 6B, the extraction column 10 may be used in conjunction with a sample port 68 as part of a sample analysis system. The sample port 68 has a proximal portion 94 configured to sealingly engage the extraction column 10 and a distal portion 96 configured to engage a component of the sample analysis system. The proximal portion 94 includes a first chamber 98 configured to receive the elongated sleeve 55 of the extraction media portion 16 of the extraction column 10. The distal portion 96 has a second chamber 100 configured to receive a component of a sample analysis system 92. The first chamber 98 is in fluid communication with the second chamber 100 via a low volume fluid passageway 104. In an embodiment, the fluid passageway 104 between the first chamber 98 and the second chamber 100 has a volume of about 0.5 microliters or less.

The first chamber 98 has an inner surface 106 that generally corresponds in size and shape with the external surface 66 of the sleeve of the extraction media portion 16 of the extraction column 10. In an embodiment, the inner surface 106 is generally frustoconical-shaped. The first chamber 98 also has a sealing surface 108 at its distal end in which the fluid passageway 104 is formed. The first chamber 98 has a depth D2 measured from the proximal end 110 of the sample port 68 to the sealing surface 108. The depth D2 of first chamber 98 is less than the length L1 of the elongated sleeve 55 of the extraction media portion 16 such that when a force is applied to the extraction column 10, such as the force applied to the extraction column 10 by a liquid delivery device 46, the outlet end 60 and external surface 66 of the elongated sleeve 55 engages and forms a seal with the inner surface 106 and/or sealing surface 108 of the first chamber 98 of the sample port 68. In an embodiment, the seal formed between the extraction column 10 and the sample port 68 allows leakage of no more than about 10% of the volume of the sample being transferred from the extraction column 10 to the sample port 68. In another embodiment, the seal formed between the liquid delivery device 46 and the extraction column 10 allows leakage of no more than about 10% of the volume of the sample being transferred from the extraction column 10 to the sample port 68 under injection pressures ranging from about 70 bar to about 200 bar.

Proximal portion 94 of the sample port 68 has an outer diameter that is less than the inner diameter of the open terminal end 70 of the collar 18 of the extraction column 10. As such, when the extraction column 10 is positioned on the sample port 68, the collar 18 will surround at least a portion of the external surface 112 of the proximal portion 94 of the sample port 68. The proximal portion 94 projects from the distal portion 96 by a distance that prevents interfering with forming the seal between the outlet end 60 of the elongated sleeve 55 and the inner surface 106 and/or sealing surface 108 of the first chamber 98 of the sample port 68.

Distal portion 96 of the sample port 68 has an outer diameter that is generally greater than the outer diameter of the proximal portion 94. The second chamber 100 of the distal portion 96 is configured to receive a component of the sample analysis system that is capable of transferring an eluted sample to the analytical device. The second chamber 100 is configured to sealingly engage the component of the sample analysis system. In an embodiment, the second chamber 100 is threaded. In an embodiment, the component received in the second chamber is tubing 114 capable of transferring an eluted sample to an analytical system. Exemplary analytical systems include a liquid chromatography system.

Example 1

Extraction columns were prepared utilizing extraction medium microcolumns formed from a porous monolith medium formed in a section of PEEK tubing. The porous monolith medium was prepared from a polymerization mixture having monomers (55 wt. % divinyl benzene and 45 wt % ethylvinylbenzene) at 37.5 wt. % of the mixture, an initiator (azobisisobutyronitrile (Dupont Vazo-64)) at 1.75 wt. % per weight of monomers, and a porogen at 62.5 wt. % of the mixture. The polymerization mixture was injected into the lumen of a section of activated tubing and allowed to polymerize for 18 hours at 76 degrees Celsius.

The inner surface of the PEEK tubing was activated prior to injection of the polymerization mixture so that the porous extraction medium would covalently bond to the inner surface of the tubing during polymerization. To activate the inner surface of the tubing, the PEEK tubing was filled with reaction solution containing a solvent, acetonitrile or propionitrile (alkyl nitrile derivatives) and an azo-class initiator such as Vazo-64 or Vazo-55 (Wakko V-70) in a concentration of 1-10%. The filled PEEK tube was then heated to a minimum of 80% of the 10-hour half life temperature, for example Vazo-55 has a 10-hour decomposition half life at 55 degrees Celsius. The reaction was allowed to proceed for 30 minutes. The reaction solution was replaced with fresh reaction solution and allowed to proceed for an additional 30 minutes. The reaction solution was removed from the tubing and the tubing was allowed to dry with a stream of nitrogen. After drying, the polymerization mixture was injected into the lumen of the activated tubing.

After the porous extraction medium polymerized, the tubing was cut to the desired length with an IDEX A-350 tubing cutter.

PEEK tubing having internal diameters of 0.75 mm, 1 mm, 0.5 mm, and 0.4 mm was utilized. The porous monolith medium was formed in the lumen of the tubing and the tubing was cut with an IDEX A-350 tubing cutter into sections having a length of 2 mm, 4 mm, 5 mm, or 6 mm to form the extraction medium microcolumns. The extraction medium microcolumns were inserted into the cavity of the extraction media portion of a column body to form extraction columns having the dimensions illustrated in Table 1. Extraction columns having the dimensions of extraction medium microcolumns 2, 3, and 4 from Table 1 were tested with bacterial samples as described below.

| Extraction Media Microcolumn No.: | Tubing Inner Diameter (mm) | Tubing Length (mm) | Tubing Volume (μl) |
|---|---|---|---|
| 1 | 0.75 | 2 | 0.9 |
| 2 | 1 | 2 | 1.6 |
| 3 | 1 | 4 | 3.1 |
| 4 | 0.4 | 6 | 0.8 |
| 5 | 0.5 | 4 | 0.8 |

Test samples were prepared from extracts of *Escherichia coli*. The extract was prepared by lysing *E. coli* in a solvent containing 50 vol. % formic acid (FA) and 25 vol. % acetonitrile (ACN). The FA and ACN concentrations were adjusted to 37.5 vol. % ACN and 25 vol. % FA. The protein concentration in the test samples was between 2 mg/ml and 3 mg/ml as determined with BCA analysis. Test samples were diluted and either 0.5 μg or 1 μg protein was applied to the extraction columns.

Before the test samples were applied to the extraction columns, the porous monolith medium was wetted with 50 μl of ACN having a 0.2 vol. % FA. The porous monolith medium was then equilibrated with 50 μl of a solution containing water and 0.2 vol. % FA. Samples having a total amount of either 0.5 μg or 1 μg protein in volumes ranging from 50 μl to 100 μl were pushed through the porous monolith medium in the extraction column. The flow through from the samples was collected for analysis. The porous monolith medium was washed with 50 μl of a solution containing water and 0.1 vol. % FA. Protein samples were eluted from the porous monolith medium with 10 μl of a solution containing water, 60 vol. % ACN, and 0.2 vol. % FA. The eluted proteins were collected for analysis.

The flow through (FT) samples and eluted samples were analyzed for protein concentration. In some results, the eluates of multiple samples (3-5) were combined and partially dried to about ⅓ their original volume before being analyzed, and the protein amount per extraction column was later calculated from the combined results. Protein concentration was determined using the Nanodrop BCA assay (Thermo Fisher Scientific). The bovine serum albumin standard curves were prepared using the same FA and ACN concentrations as was used in the FT and eluate samples. The results are provided in Table 2.

The FT and eluate samples were then analyzed by SDS-PAGE. The FT and eluate from 5 samples was combined and dried before analysis. The samples were run on a gel having a gradient from 4% to 20%. The gel was then silver stained and analyzed. The results (not shown) were consistent with protein assay results.

Figure 8A:
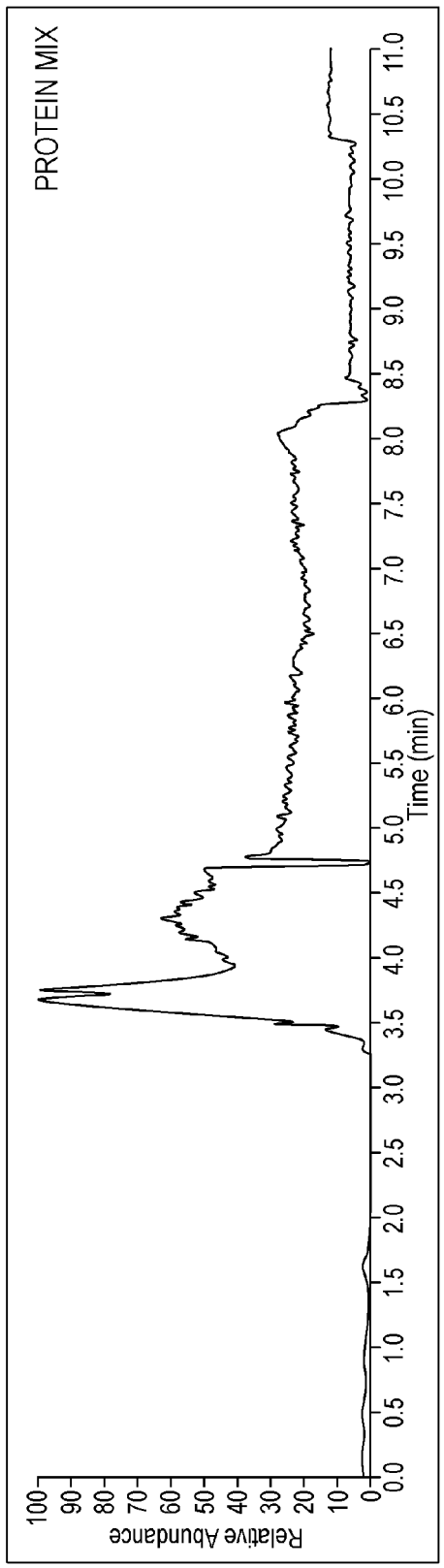
FIG. 8A is a chromatogram obtained from a sample containing a mixture of 5 proteins eluted from an extraction column in accordance with embodiments of the invention.
Figure 8B:
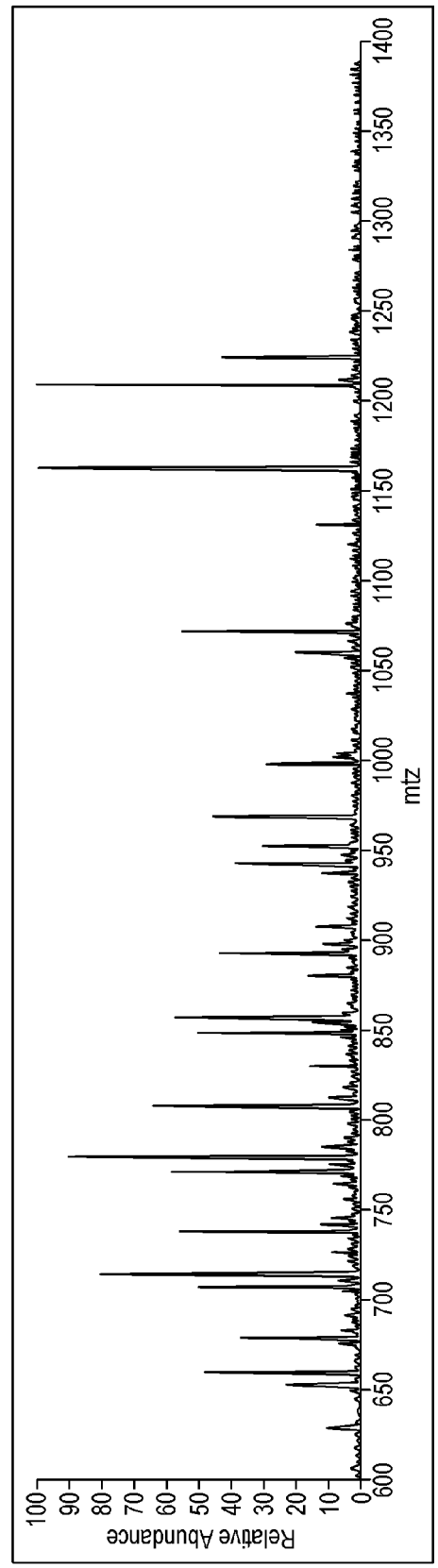
FIG. 8B is a mass spectrum obtained from a sample containing a mixture of 5 proteins eluted from an extraction column in accordance with embodiments of the invention.
Figure 9:
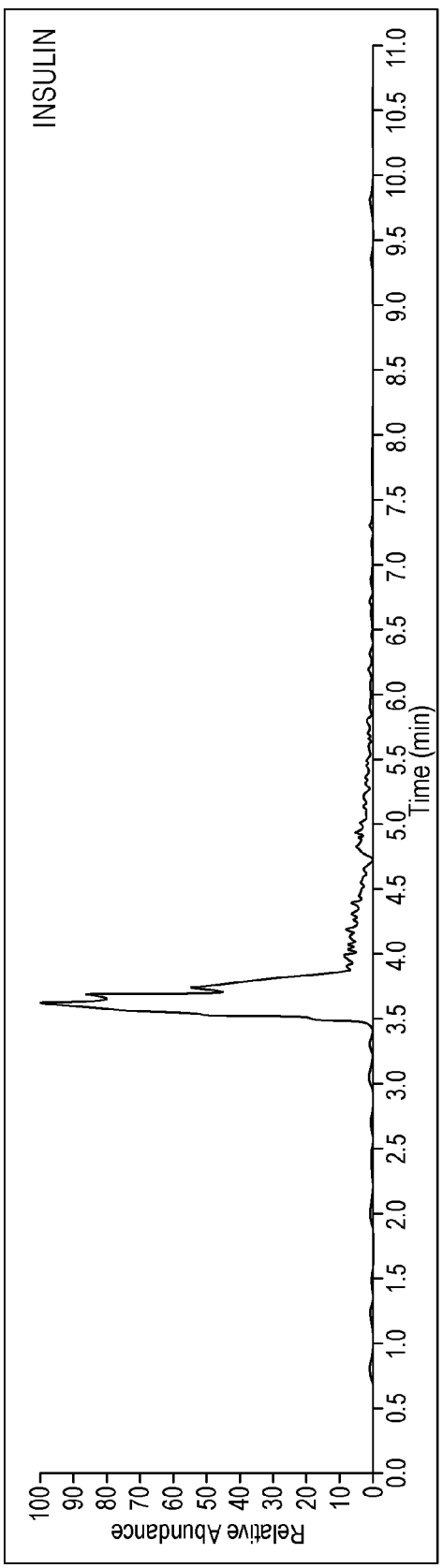
FIG. 9 is a chromatogram of insulin obtained from a sample eluted from an extraction column in accordance with embodiments of the invention.
Figure 10:
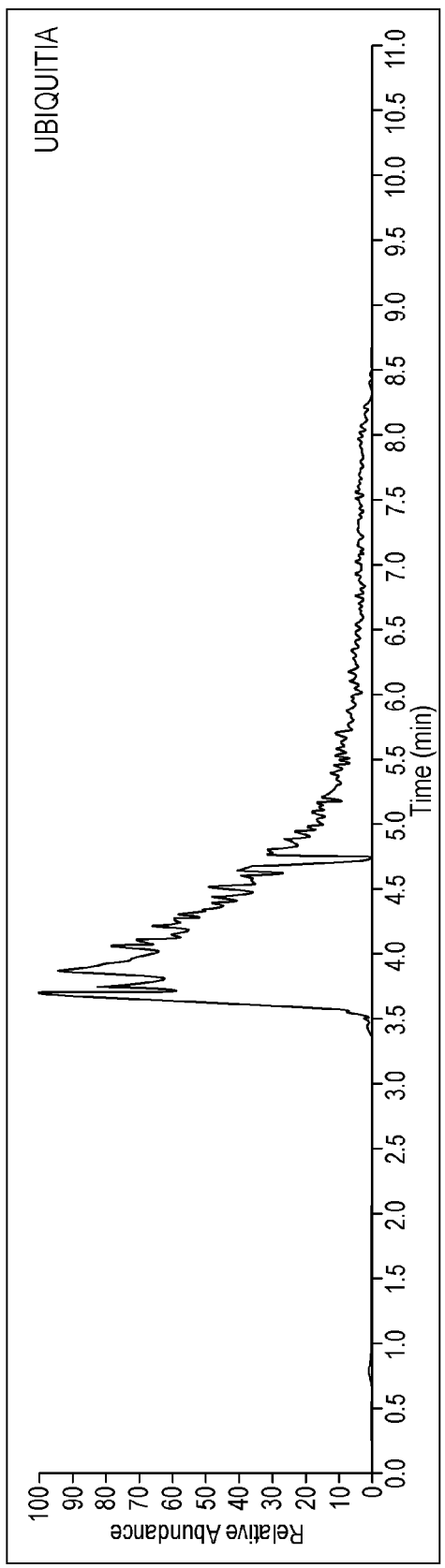
FIG. 10 is a chromatogram of ubiquitin obtained from a sample eluted from an extraction column in accordance with embodiments of the invention.
Figure 11:
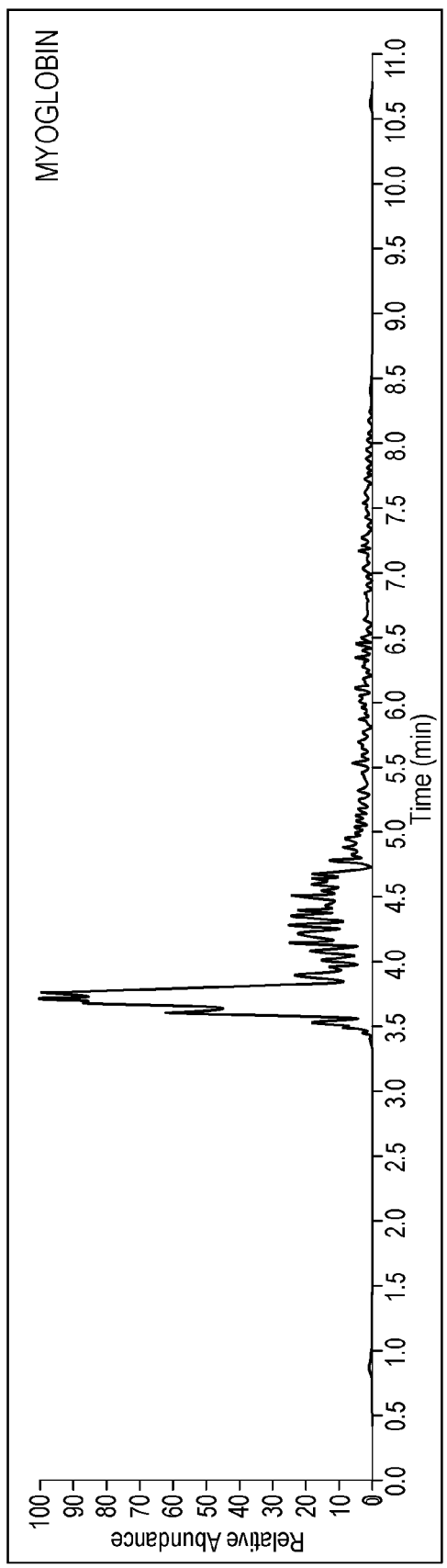
FIG. 11 is a chromatogram of myoglobin obtained from a sample eluted from an extraction column in accordance with embodiments of the invention.
Figure 12:
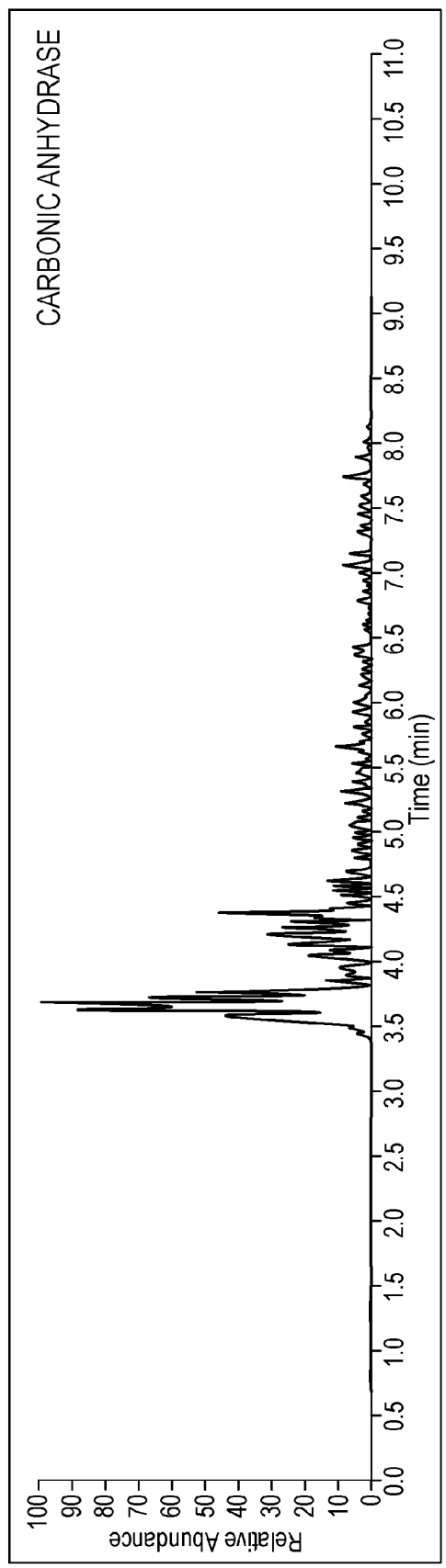
FIG. 12 is a chromatogram of carbonic anhydrase obtained from a sample eluted from an extraction column in accordance with embodiments of the invention.

In a further test, during the elution step, the extraction column was inserted into a sample port of a liquid chromatography system and eluted with an aqueous solution containing 50 vol. % ACN and 0.2 vol. FA at a rate of 1.5 μl/min. FIG. 8A is a chromatograph obtained from the eluted sample from the protein mix. FIG. 8B is a mass spectrograph obtained from the eluted protein mix. FIG. 9 is a chromatograph obtained from the eluted insulin sample. FIG. 10 is a chromatograph obtained from the eluted ubiquitin sample. FIG. 11 is a chromatograph obtained from the eluted myoglobin sample. FIG. 12 is a chromatograph obtained from the eluted carbonic anhydrase sample.

While the present invention has been illustrated by the description of one or more embodiments thereof, and while the embodiments have been described in considerable detail, they are not intended to restrict or in any way limit the scope of the appended claims to such detail. Additional advantages and modifications will readily appear to those skilled in the art. The invention in its broader aspects is therefore not limited to the specific details, representative apparatus and method and illustrative examples shown and described. Accordingly, departures may be from such details without departing from the scope or spirit of the general inventive concept.

| Microcolumn No.: | Tubing length (mm) | Tubing vol. (μl) | Sample prot. (μg) | Sample vol. (μl) | Eluted (μg) | Yield % (eluted μg/ applied μg) | Eluted (μg)/ tip vol. (μl) |
|---|---|---|---|---|---|---|---|
| 2 | 2 | 1.6 | 0.55 | 50 | 0.35 | 64% | 0.22 |
| 3 | 4 | 3.1 | 0.55 | 50 | 0.34 | 62% | 0.11 |
| 2 | 2 | 1.6 | 1.67 | 100 | 0.8 | 48% | 0.51 |
| 3 | 4 | 3.1 | 1.67 | 100 | 0.56 | 34% | 0.18 |
| 4 | 6 | 0.8 | 1 | 50 | 0.27 | 27% | 0.36 |

Example 2

Figure 7:
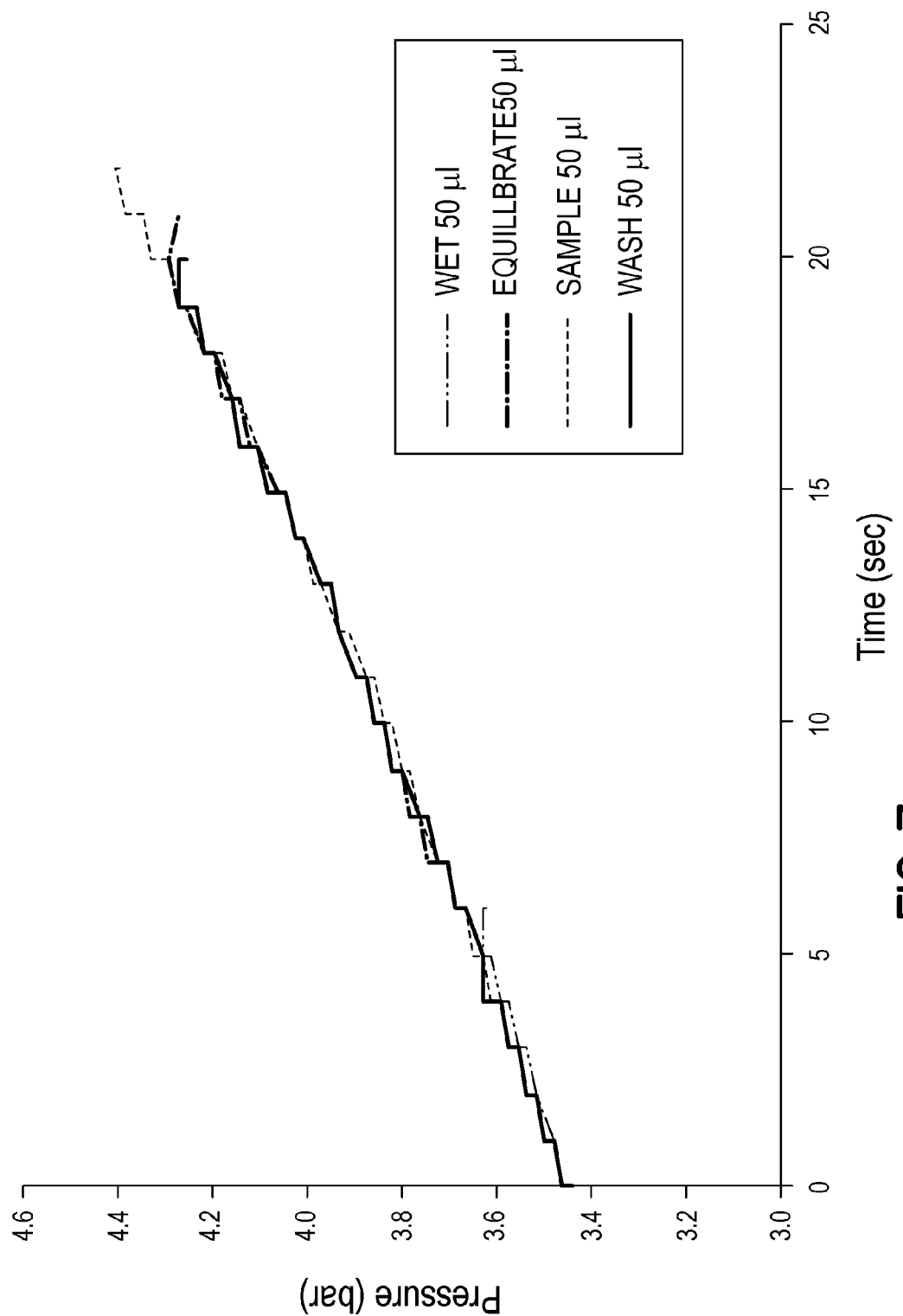
FIG. 7 is a graph of the backpressures in the extraction column during liquid passage through the porous extraction medium.

Samples containing mixture of proteins including insulin, ubiquitin, myoglobin, carbonic anhydrase, and bovine serum albumin were prepared in a solution having 37.5 vol. % ACN and 25 vol. % FA. The total protein in the samples was 0.5 μg. The samples were tested on an extraction column which was prepared as described above in Example 1 having the dimensions for Extraction Column No. 5 in Table 1. The porous extraction media of the extraction columns were wetted and equilibrated, the samples were applied, and the porous extraction media in the extraction columns were washed as described above in Example 1. In an initial round of tests, samples were manually eluted while monitoring the pressure inside of the extraction tip. It was observed that 50 μl samples may be pushed through the extraction column in less than 15 seconds and, as illustrated in FIG. 7, that backpressure created in the tip may be used to monitor the moment when all of the liquid has passed through the porous extraction medium.

An autosampler was then used to pass liquids through the extraction column. The force applied by the liquid delivery probe was measured to identify the amount of forced needed to form a seal between the liquid delivery device and the extraction column as well as between the extraction column and the sample port to a liquid chromatography system. Of particular concern is forming a seal between these components under the high operating backpressures of liquid chromatography systems that typically range from about 70 bar to about 200 bar. It was observed that a force of 30 N applied to the extraction column by the liquid delivery probe was sufficient to form a seal between the components at a backpressure of 210 bar.

What is claimed is:

1. An extraction column, comprising:
a column body having a reservoir portion, an extraction media portion, and a collar portion;
wherein the reservoir portion includes an inlet and a reservoir, and the extraction media portion includes an elongated sleeve having an inner surface defining a cavity for containing an extraction medium with an inlet end in fluid communication with the reservoir and an outlet end disposed remote from the inlet end,
and further wherein the collar portion extends axially in a common direction with the elongated sleeve and has a terminal end which is spaced apart from the outlet end of the elongated sleeve and which extends axially at least to a plane defined by the outlet end of the elongated sleeve;
the extraction column further comprising an extraction medium within the cavity and extending substantially to the outlet end of the elongated sleeve.

2. The extraction column of claim 1, wherein the reservoir includes a sealing surface in fluid communication with the cavity of the extraction media portion.

3. The extraction column of claim 1 further providing a fluid passageway between the reservoir and the cavity of the extraction media portion, wherein the fluid passageway has a diameter that is less than the diameter of the cavity of the extraction media portion.

4. The extraction column of claim 3 wherein the fluid passageway is generally frustoconical-shaped with an angle of convergence of less than about 10 degrees.

5. The extraction column of claim 3 wherein the fluid passageway has a volume that does not exceed about 1000 nl.

6. The extraction column of claim 1, wherein the terminal end of the collar portion extends axially beyond the plane defined by the outlet end of the elongated sleeve.

7. The extraction column of claim 1, wherein the terminal end of the collar portion extends axially beyond the plane defined by the outlet end of the elongated sleeve by a distance sufficient to prevent contact of the outlet end of the elongated sleeve by any portion of a second extraction column.

8. The extraction column of claim 1 wherein the reservoir portion inlet has an inner diameter, the terminal end of the collar portion has an outer diameter and the inner diameter of the inlet is not greater than the outer diameter of the terminal end of the collar portion.

9. The extraction column of claim 8 wherein the inner diameter of the inlet is less than the outer diameter of the terminal end of the collar portion.

10. The extraction column of claim 1 further comprising a shoulder projecting outwardly from the reservoir portion adjacent the inlet.

11. The extraction column of claim 1, wherein the reservoir includes a sealing surface that is funnel-shaped and comprises an annular wall that tapers inwardly toward the extraction media portion.

12. The extraction column of claim 1, wherein reservoir is defined by an inner surface that includes a first portion proximal to the inlet and a second portion proximal the extraction media portion, the first portion has a first proximal end that corresponds with the inlet and a first distal end adjacent the second portion and a first angle of convergence calculated as the difference between the inner diameters of the first reservoir portion at the first proximal end and the first distal end, the second portion has a second proximal end adjacent to the first distal end and a second distal end proximal to the extraction media portion and a second angle of convergence calculated as the difference between the inner diameters of the second reservoir portion at the second proximal end and the second distal end, and the angle of convergence of the first portion is less than the angle of convergence of the second end.

13. The extraction column of claim 12 wherein the second portion is funnel-shaped and comprises an annular wall that tapers inwardly toward the extraction media portion.

14. The extraction column of claim 1 wherein the cavity of the elongated sleeve is generally frustoconical-shaped with an angle of convergence of less than about 1 degree.

15. The extraction column of claim 1 wherein the extraction media portion has an external surface configured to form a seal with an injection port of a sample analysis system.

16. The extraction column of claim 1 wherein the extraction media portion has an external surface has a generally frustoconical shape.

17. The extraction column of claim 1 wherein extraction medium is a solid phase extraction medium.

18. The extraction column of claim 17 wherein the solid phase extraction medium is a porous solid polymer defining a polymer monolith.

19. The extraction column of claim 18 wherein the extraction medium is included in a generally cylindrical sheath that is open at both ends and having an outer surface with a diameter that corresponds to a diameter of the inner surface of the cavity of the elongated sleeve.

20. The extraction column of claim 19 wherein the sheath is a section of a tube.

21. The extraction column of claim 19 wherein the sheath is comprised of polyethylene ether ketone, fused silica, fluoro-polymers, and cyclic olefin copolymers.

22. The extraction column of claim 19 wherein the extraction medium is covalently linked to the inner surface of the cavity of the polymer sheath.

23. The extraction column of claim 1 wherein the extraction medium includes a plurality of non-porous beads, porous beads, or a mixture thereof.

24. The extraction column of claim 23 further comprising a first frit proximal the inlet end of the elongated sleeve and a second frit proximal the out end of the elongated sleeve.

25. A system for extracting a desired fraction from a liquid comprising an extraction column from claim 1 and a sample port having a first chamber configured to receive the elongated sleeve of the extraction column.

26. The system of claim 25 further comprising a liquid delivery device.

27. The system of claim 26 wherein the liquid delivery device is a ceramic probe.

28. The system of claim 25 further comprising an analytical device.

29. The system of claim 28 wherein the analytical device is selected from the group consisting of a mass spectrometer, a liquid chromatography device, and combinations thereof.

30. The system of claim 25 wherein the sample port further includes a second chamber configured to receive tubing from the analytical device and a fluid passageway between the first chamber and the second chamber.

31. The system of claim 30 wherein the fluid passageway has a volume that is not greater than about 0.5 µl.

32. The system of claim 25 wherein the sample port includes an outer surface extending generally parallel to the axis of the first chamber, wherein the outer surface has a diameter that is less than an inner diameter of the collar portion of the extraction column.

33. The extraction column of claim 1 wherein the column body is discrete from the column body of other extraction column.

34. The extraction column of claim 1 wherein the column body is formed from a single piece of material.

* * * * *